(12) United States Patent
Pologe et al.

(10) Patent No.: US 8,078,251 B2
(45) Date of Patent: Dec. 13, 2011

(54) SPRING WING ASSEMBLY FOR PHOTOPLETHYSMORGRAPHIC SENSOR

(75) Inventors: Jonas Alexander Pologe, Boulder, CO (US); Theodore Philip Delianides, Boulder, CO (US)

(73) Assignee: Kestrel Labs, Inc., Boulder, CO (US)

( * ) Notice: Subject to any disclaimer, the term of this patent is extended or adjusted under 35 U.S.C. 154(b) by 1574 days.

(21) Appl. No.: 11/473,092

(22) Filed: Jun. 22, 2006

(65) Prior Publication Data

US 2007/0299329 A1 Dec. 27, 2007

(51) Int. Cl.
*A61B 5/1455* (2006.01)
(52) U.S. Cl. ......... 600/338; 600/322; 600/326; 600/344
(58) Field of Classification Search .......... 600/309–344, 600/383, 545
See application file for complete search history.

(56) References Cited

U.S. PATENT DOCUMENTS

| | | | |
|---|---|---|---|
| 3,827,428 A | 8/1974 | Hon | |
| 5,154,175 A | 10/1992 | Gunther | |
| 5,228,440 A | 7/1993 | Chung | |
| 5,361,757 A | 11/1994 | Smith | |
| 5,419,322 A * | 5/1995 | Joseph et al. | 600/338 |
| 5,911,690 A * | 6/1999 | Rall | 600/313 |
| 6,298,253 B1 * | 10/2001 | Buschmann | 600/338 |
| 6,690,958 B1 * | 2/2004 | Walker et al. | 600/323 |
| 2005/0033130 A1 * | 2/2005 | Rall et al. | 600/338 |
| 2005/0283059 A1 | 12/2005 | Iyer | |
| 2007/0260130 A1 * | 11/2007 | Chin | 600/323 |

* cited by examiner

*Primary Examiner* — Eric Winakur
*Assistant Examiner* — Chu Chuan (JJ) Liu

(57) ABSTRACT

A photoplethysmographic sensor designed for use on the presenting portion of a fetus during labor and delivery. The sensor has a non-deployed state in which the sensor presents a smaller footprint, or cross sectional area, for transvaginal insertion. Once the sensor is applied to the fetal tissue it is moved into the deployed state, which has a larger footprint or cross sectional area, than the sensor does in the non-deployed state. The deployed state optimizes the physical distance between the light emitter and the photodetector to maximize the photoplethysmographic measurement accuracy from the fetal tissue.

18 Claims, 4 Drawing Sheets

SPRING WING ASSEMBLY FOR PHOTOPLETHYSMORGRAPHIC SENSOR

STATEMENT OF GOVERNMENT INTEREST

This invention was made with government support under R44 HL081866 awarded by National Institutes of Health. The government has certain rights in the invention.

BACKGROUND OF THE INVENTION

The present invention relates generally to the field of fetal monitoring and more specifically to the photoplethysmographic measurement of oxygen saturation and heart rate from a fetus during labor and delivery.

Pulse oximeters are commonly used in adult, pediatric, and neonatal care to provide a measurement of arterial oxygen saturation. A pulse oximetry system typically consists of a sensor which is applied to the patient, a monitor on which the measurements of arterial oxygen saturation are displayed, and a cable which connects the sensor to the monitor. The sensor typically contains light emitting diodes whose output light is incident on the surface of the tissue-under-test and a photodetector that measures the intensity of the light exiting the tissue-under-test at the sensor site.

The sensor does not necessarily have to contain the emitters for the delivery of light to the tissue-under-test. Light can be transmitted to the sensor from the emitters via optical fibers. The use of one or more optical fibers allows the emitters to be located some distance from the sensor. Light from the emitters can be coupled into the fibers, and the distal ends of the fibers, located in the sensor, become the light emitter. It is also possible to use optical fibers as the photodetector for receiving light from the tissue-under-test, but this tends to result in a very small signal level compared to placing a photodetector, such as a photodiode, directly on the surface of the skin.

The sensor cable must contain the electrical and/or optical conductors for powering the light emitters and for conducting the electrical or optical signals from the photodetector back to the monitor for analysis and conversion to the measured parameters. If the LEDs and photodiode reside in the sensor, the conductors will be electrical wires. If the emitters and/or photodiode (or other similar device, such as a phototransistor, for conversion of the detected light to an electrical signal) reside somewhere other than directly in the sensor, the conductors will be optical fibers or a mixture of electrical and optical conductors.

While arterial oxygen saturation is the most commonly measured blood analyte, it is only one of several blood analytes that are, or can be, measured by photoplethysmography, the monitoring technology used in pulse oximetry. Other blood analytes that can be measured include carboxyhemoglobin and methemoglobin. Hemodynamic parameters measured by photoplethysmography include heart rate and perfusion index, an indicator of the blood perfusion of the tissue-under-test at the sensor site. The tissue-under-test is the tissue that the light emitted from the sensor passes through before being detected by the photodetector.

The use of pulse oximetry has recently been expanded to include its use on a fetus during labor and delivery. U.S. Pat. No. 5,228,440 reveals a fetal pulse oximetry sensor which is intended to be positioned on the fetal cheek or side of the fetal head. This sensor does not adhere to the fetus and is therefore sensitive to changing position with respect to the fetus as a result of contractions during labor and progression of the fetus through the birth canal. This movement of the sensor with respect to the tissue-under-test often results in a loss of signal, thereby necessitating periodic repositioning of the sensor. In addition, the application of the light emitter and the photodetector to the same surface of the tissue-under-test, versus placement across the tissue-under-test such as when the light emitter and the detector in the sensor are placed on opposite sides of a finger, allows the possibility of the emitted light being shunted directly from the light emitter to the photodetector without passing through the tissue-under-test. This can cause the fetal pulse oximetry readings to be erroneous.

Alternate methodologies for fetal pulse oximetry have been considered that make use of a modified version of the fetal spiral electrode, a device designed and manufactured for the measurement of the fetal electrocardiogram (ECG). This spiral ECG electrode is disclosed in FIGS. 8, 9, and 10 of U.S. Pat. No. 3,827,428. The spiral, or more accurately "helical", ECG electrode in combination with fetal pulse oximetry has been presented in a number of different potential configurations.

In U.S. Pat. No. 5,154,175 the helical electrode is used to hold the light emitter and photodetector elements flush against the fetal scalp, the tissue-under-test. While this sensor remains fixed with relation to the fetus, it still has the problem that both the light emitter and the photodetector lay on the same surface of the tissue-under-test. This allows the possibility of errors in readings caused by light being shunted directly from the emitter to the detector without passing into or through the tissue-under-test.

Two patent documents, U.S. Pat. No. 5,361,757 and U.S. Patent Application Publication No. 2005/0283059 A1, disclose a potential solution to this problem. In the first of these two publications, the emitters are light emitting diodes (LEDs) which are positioned at a window in the helical needle. When the sensor is in position on the fetal scalp, the light is emitted subcutaneously into the tissue-under-test and detected when it emerges from the tissue at a detector in the base of the sensor on the surface of the fetal scalp. U.S. Publication No. 2005/0283059 A1 reveals a slightly different arrangement in which both the LEDs and the photodetector are positioned in the helical needle. In this arrangement the light is transmitted subcutaneously from the light emitters directly across to the photodetector, given that both elements are located under the surface of the skin once the sensor is in place on the fetus.

The problem common to both of these solutions is the extremely short pathlength that the light traverses in the tissue-under-test before reaching the photodetector. Photoplethysmography requires that the light passing through the tissue-under-test be modulated by the pulsating blood flow thereby creating a pulsatile light signal at the photodiode. With the extremely short physical pathlength of these previous sensor configurations, the light passes through very little pulsatile tissue which results in a very small pulsatile signal. The end result is a poor signal-to-noise ratio and inaccurate photoplethysmographic readings. It is necessary to have a sufficiently long pathlength for the light to traverse the tissue-under-test to create a large pulsatile component in the received light signal for calculation of the measurement parameters.

Designing a fetal sensor that provides a sufficiently large pathlength through the tissue-under-test, typically the fetal scalp, creates a new problem because it necessitates a large physical size for the sensor. The fetal sensor is intended for use during labor and delivery and preferably such a sensor would be placed on the fetus as early in the progression of labor as possible. If the sensor is large, it requires greater dilation of the cervix before it can be placed on the fetus. The greater the dilation required for sensor placement, the longer the clinician must wait during labor before the sensor can be placed and the less valuable a clinical tool it becomes.

The solution to the problem of how to create a fetal sensor with a sufficiently long tissue pathlength, while still minimizing the size of the sensor during insertion to allow early placement, is the subject of this invention.

BRIEF SUMMARY OF THE INVENTION

It is the object of this invention to provide a sensor for fetal monitoring which can be placed on the fetus early in the course of labor and which can produce photoplethysmographic signals with a high signal-to-noise ratio allowing accurate measurement of one or more blood analyte levels or one or more hemodynamic parameters.

The current embodiment of this invention is a fetal oximetry sensor with a sensor body designed to adhere to the fetal tissue and which incorporates a set of wings which deploy outward from the sensor body after the sensor body is in place for monitoring. In the preferred embodiment the means by which the sensor body adheres to the tissue is through the use of a helical needle similar in design to that of the fetal spiral electrode commonly used to measure the fetal ECG.

One or more optical fibers running through the inside of the helical needle deliver light to the tip of the needle where it is emitted into the fetal tissue. One of the wings houses a photodetector which, when the wing is in the deployed state, positions the photodetector against the fetal tissue.

The wings serve several crucial functions. One function is to hold the photodetector flush against the surface of the fetal scalp with minimal pressure to ensure that there is flush contact between the photodiode and the tissue-under-test while also ensuring that the local perfusion is not impeded.

Another purpose of the wing is to optimize the physical pathlength through the tissue-under-test by setting the photodetector at an optimal distance from the light emitters, which in this embodiment are the distal ends of one or more optical fibers positioned at the tip of the helical needle. Increasing the pathlength between these two elements increases the pulsatile portion of the received photoplethysmographic signal but decreases the overall signal amplitude. Choosing an optimal pathlength balances these two parameters to ensure that the overall signal amplitude is within the operating range of the photoplethysmographic monitor with which the sensor will be designed to operate while maximizing the pulsatile portion of the signal to allow the most accurate possible photoplethysmographic measurements.

Because the optimal pathlength is typically at least one centimeter, a solid (symmetrical) sensor body large enough to hold a photodiode at the required distance from the helical needle would be significantly larger than two centimeters in diameter. One problem with the application of such a large sensor when applied to a fetus transvaginally, meaning through the vaginal opening, is that it must be applied later in the labor process when the cervix has dilated sufficiently to accommodate a sensor of this size.

In the current invention, by placing the photodiode on a movable wing, the wing can be folded against the sensor body to pass through the cervix and then deployed to the optimal distance from the point at which the light exits the sensor after the sensor is affixed to the fetal tissue. Prior to deploying the wing or wings the sensor presents a smaller cross sectional area to the cervix than it does after deployment, which allows the sensor to be placed on the fetus as early as possible during labor.

The inclusion of one or more additional wings to the sensor helps stabilize the sensor body once the wings are deployed. With only one wing it is difficult to apply downward pressure to the photodetector without misaligning the needle and sensor body. With two or more wings positioned radially around a central sensor body adhered to the tissue-under-test, the downward pressure of the wings balance against each other and stabilize the sensor in its upright position.

DETAILED DESCRIPTION OF THE INVENTION

Placing a sensor during labor transvaginally on a fetus presents several unique challenges. The maternal tissues typically block the view of the fetus and in the early stages of labor, the cervix provides only a small orifice through which the insertion and placement of the sensor must be performed. In direct contrast to these constraints, a fetal oximetry sensor requires a physical separation of about one centimeter or greater between the light emitter and the photodetector on the tissue-under-test to obtain accurate readings. The current embodiment of this invention addresses these issues allowing transvaginal insertion of a fetal oximetry sensor through the cervix in early labor while still providing the optimal light emitter to photodetector separation distance while monitoring.

Figure 1A:
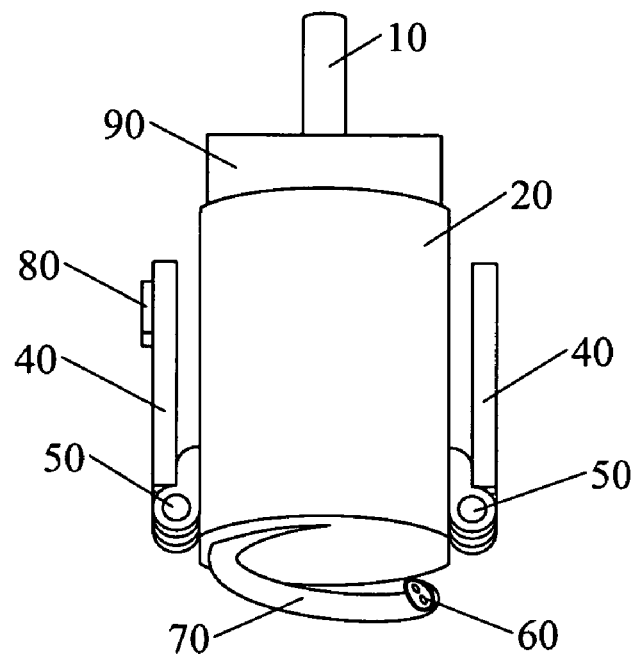
FIG. 1. Fetal Oximetry Sensor, Hinged Wing Configuration: The sensor is shown in the non-deployed and deployed states. This sensor design utilizes a helical needle based light emitter.
Figure 1B:
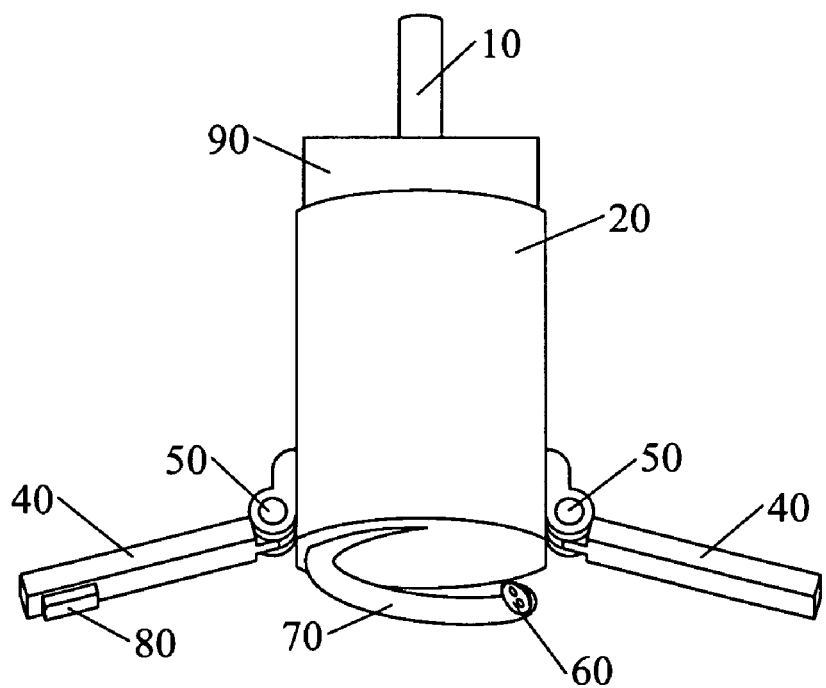

FIGS. 1A and 1B show one embodiment of this sensor in the non-deployed and the deployed states, respectively. The non-deployed state is the state in which the sensor would be passed through the vagina and the cervix to the fetal tissue. This sensor consists of a cable 10 housing electrical and optical conductors for carrying electrical or optical signals to and from the sensor. In the configuration of the sensor shown in these figures, the conductors would include two electrical wires connected to the photodetector 80 and one or more optical fibers to deliver light to the tip 60 of the helical needle 70. Two additional conductors in the cable 10 would be electrical wires that connect to the ECG contacts created by the metal surface of the helical needle 70 and the reference electrode 90.

The optical fiber (or fibers) at the needle tip 60 is the light emitter in this configuration of the sensor. It is at this point where the light in the optical fiber or fibers exits the sensor and enters the tissue-under-test. The tissue-under-test is typically the fetal scalp although other fleshy, well-vascularized sites on the fetus could provide an appropriate sensor site.

The sensor body 20 contains a helical needle that extends from the base of the sensor body, which provides a means for adhering the sensor to the tissue-under-test. As in the conventional fetal spiral electrodes used for monitoring fetal ECG, the helical needle in the fetal oximetry sensor is rotated into the fetal tissue to attach or adhere the sensor to the fetus. The use of the helical needle to adhere the sensor body, and therefore the sensor, to the tissue-under-test is the preferred embodiment but it is only one of many different methods that can be used.

Another methodology to adhere or attach the sensor to the tissue-under-test is shown in the sensor depicted in FIG. 2 where suction applied to a cup-shaped depression 120 at the base of the sensor body provides the force necessary to adhere the sensor to the tissue-under-test. In this configuration a small diameter tube 130 extends from the suction cup 120 in the base of the sensor body to an external pump located in the monitor which draws a vacuum to hold the sensor in place.

The helical needle with its integral optical fibers as shown in FIGS. 1A and 1B is preferred because this design allows the subcutaneous delivery of light to the tissue-under-test. Since the helical needle is rotated into the tissue, the light emitted must pass through the tissue-under-test before being received by the photodetector 80 which lies against the surface of the tissue-under-test once the deployable wings 40 are positioned in the deployed state as shown in FIG. 1B. This design eliminates the possibility of light being shunted directly from the light emitter to the photodetector without passing through the tissue-under-test, which creates erroneous readings. In photoplethysmographic instruments such as pulse oximeters, the photodetector is typically a photodiode because these devices have high responsivity to incident light, low noise levels, and allow for a large surface area to be in contact with the tissue-under-test, thereby providing a large received signal level. The photodetector functions to convert the received light signals, from the tissue-under-test, into electronic signals that are processed by the photoplethysmographic instrument, to which the sensor is connected, to allow calculation of the desired blood analytes or hemodynamic parameters.

The sensor in the non-deployed state as shown in FIGS. 1A, 2A, 3A and 4A, present a small cross sectional area during insertion of the sensor. That is, with the wings or other such deployable member in the non-deployed state, the sensor can be inserted through a cervix which is considerably less dilated than would be possible with the deployable member in a fully deployed state. The sensor in the deployed state is shown in FIGS. 1B, 2B, 3B, and 4B. In the deployed state the deployable members 40 pivot outward from the pivot point 50 to position the photodetector 80 against the tissue-under-test. In this deployed position the sensor is set to function as a photoplethysmographic sensor capable of sensing various different blood analyte levels or hemodynamic parameters.

The pivot 50 is the point at which the deployable members are moveably attached to the sensor body. The pivot can be any one of a number of different possible elements. One additional goal of the pivot, however, is to create a gentle downward force between the deployable members and the surface of the tissue-under-test. This downward force ensures flush contact between the active elements in the deployable members, such as the photodetector or the light emitter, and the tissue-under-test. The downward pressure should be light enough to prevent voiding the local blood perfusion at the points of contact with the tissue. The pivot element, or elements in the case where multiple deployment members are used, could be a hinge, possibly with an integral spring to apply the required downward force or spring force against the tissue-under-test. The pivot element could also be a "living hinge" where the plastic of the deployable member has a thin section that acts as the pivot and simultaneously applies a downward force due to the "memory" of the angle at which the living hinge was molded.

Figure 4A:
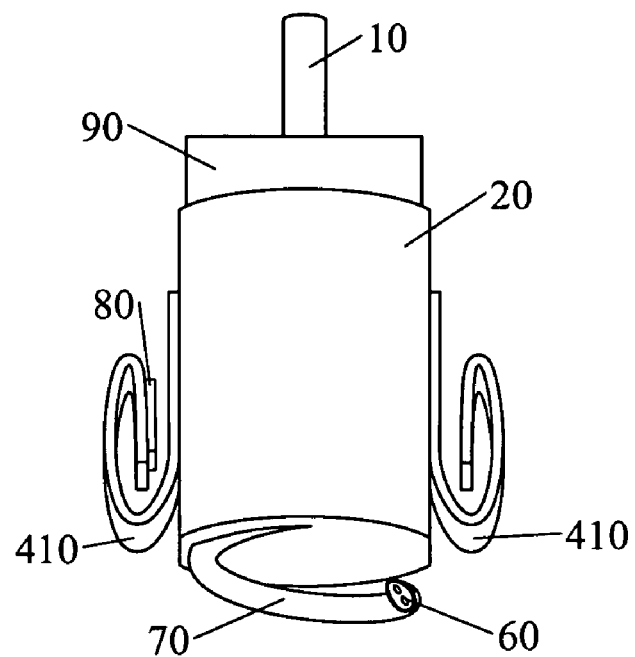
FIG. 4. Fetal Oximetry Sensor, Shape Memory Deployment: A shape memory element deploys the wings, or deployable members, upon warming to body temperature. The sensor is shown in the non-deployed (at storage temperature) and deployed (at body temperature) states.
Figure 4B:
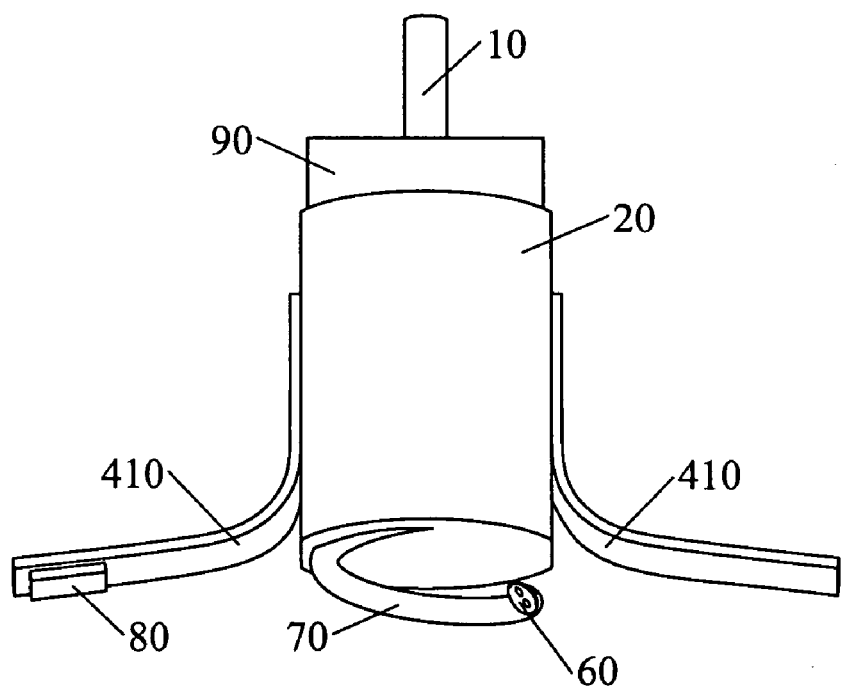

Another alternative is for the deployable member to be made of a shape memory alloy. This embodiment of the sensor is shown in FIGS. 4A and 4B in the non-deployed and the deployed states, respectively. In this case the deployable member 410 would shift from the non-deployed state to the deployed state when warmed by body heat after being applied to the fetal tissue. A unique element of this embodiment is that the deployable member does not require additional external manipulation for deployment of the wings. Once the sensor is in place on the fetus the deployable members will move into place as the sensor warms to body temperature, typically 37 degrees Celsius. In this configuration of the sensor, the deployable member 410 acts as both the deployable member and the pivot point, thereby providing the movable attachment between the deployable member and the sensor body.

Shape memory alloy materials include nickel titanium (NiTi) and copper zinc aluminum (CuZnAl) among others. These shape memory alloys undergo a reversible phase transformation when the temperature of the material changes. Selection of an alloy with a phase change just below body temperature, but above room temperature, allows the deployable members to maintain the non-deployed state until the sensor is in place on the fetus. Thus the phase change temperature would be selected to be between 27 and 37 degrees Celsius.

One problem with the embodiments of the sensor shown in FIGS. 1 and 2 is that the wings deploy, as depicted in the drawings, in a downward manner. With this method of deployment, it is likely that even if the sensor body is applied correctly to the fetus some maternal tissue may intercede between the deployable member or members and the fetus once the wings are deployed. To achieve accurate measurements on the fetus, the clinician would have to manually clear the maternal tissue from under the deployed members.

Figure 3A:
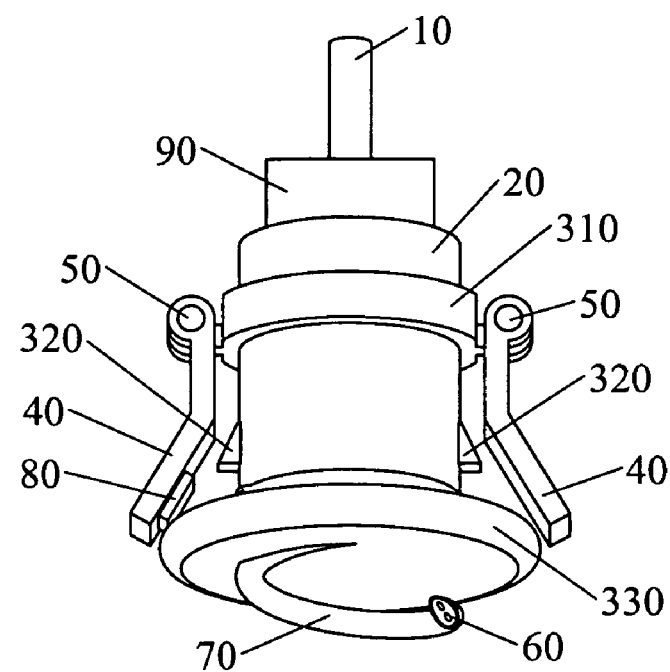
FIG. 3. Fetal Oximetry Sensor, Slip Ring Configuration: The sensor is shown in the non-deployed and deployed states. The ring portion of the sensor body slips down the central portion of the sensor body to deploy the wings.

To resolve this problem the deployment scheme depicted in the sensor configuration shown in FIG. 3 was developed. In this scheme the deployable members 40 are hinged to a moveable ring 310 which can slide down the sensor body. In the non-deployed state the ring 310 is near the top of the sensor body 20 and the deployable members 40 are folded tightly against the sensor body, minimizing the cross-sectional area presented to the transvaginal insertion of the sensor. The sensor in the non-deployed state is shown in FIG. 3A.

Figure 3B:
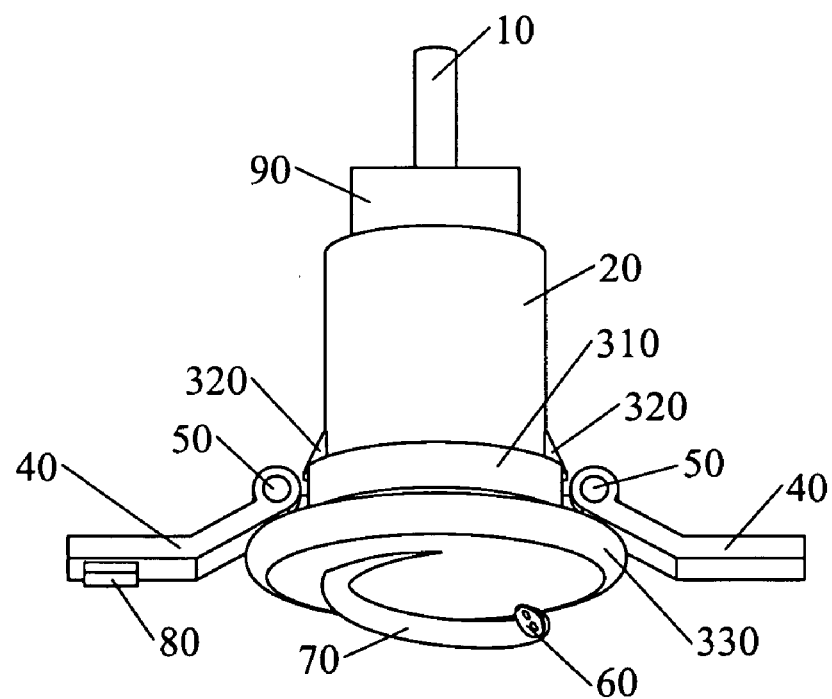

The sensor is passed through the vagina and the cervix in the non-deployed state and the helical needle 70 is rotated into place on the fetus. Once the sensor is in place the ring 310 is driven down the sensor body 20 passing over the locking tabs 320 and locked into place against the base of the sensor body. As the ring moves down the sensor body, the deployable member or members are deflected outward by the flare 330 at the base of the sensor body. Because the deployable members 40 move outward from the base of the sensor body 20 they do not trap maternal tissue under them as they are deployed. Instead this arrangement separates the maternal tissue and the fetal tissue as the wings 40 are deployed by sliding against the surface of the skin of the fetus during deployment. FIG. 3B shows this version of the sensor in the fully-deployed position.

Figure 2A:
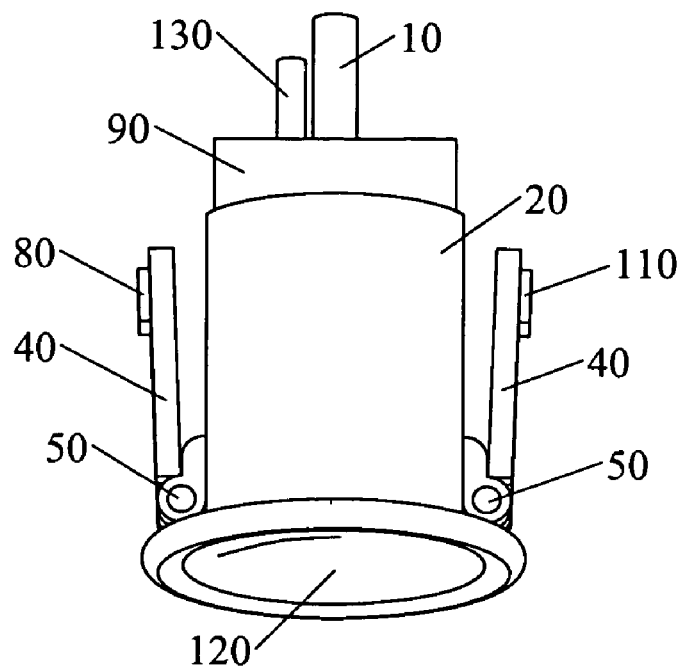
FIG. 2. Fetal Oximetry Sensor, Hinged Wing Configuration with Vacuum Attachment: The sensor is shown in the non-deployed and deployed states. This sensor design places the light emitter and photodetector on opposing wings.
Figure 2B:
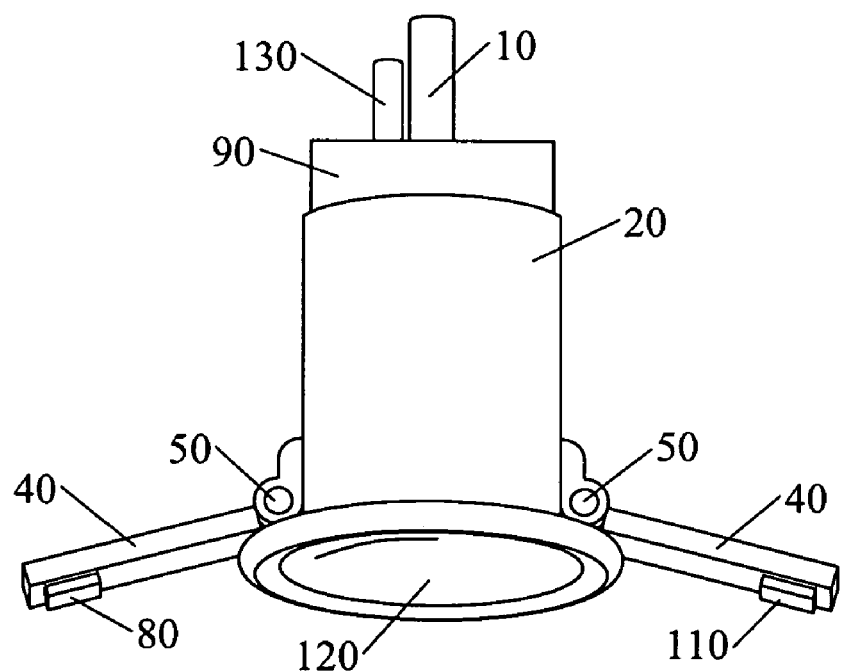

While the preferred configuration of the sensor has the light emitter at the tip of the needle, where the light can be delivered to the tissue-under-test subcutaneously as shown in FIG. 1, it is also feasible to place the light emitter on one of the deployable members. A sensor of this design is shown in FIGS. 2A and B where the light emitter 110 is housed on one of the deployable members and the photodetector 80 is housed on another. When the light emitter is positioned on the deployable member, LEDs might be used as the light sources rather than optical fibers coupled to external emitters. If LEDs housed in a deployable member are used as the light source for the sensor, the signals driving the light emitter will be electrical and the conductors carrying the drive signals for the LEDs will be electrical wires.

An additional possible configuration is to place the light emitter at the base of the sensor body and to position the photodetector on the deployable member or, similarly, to place the photodetector at the base of the sensor body and to position the light emitter on the deployable member.

While the drawings included in this patent only show sensors having two deployable members, sensor configurations with only one or with three or four deployable members are also feasible. The use of three deployable members may be preferred because three deployable members positioned radially around the sensor body, when deployed, would tend to evenly support the sensor body in an upright position between them.

The previous discussion of the invention has been presented for the purposes of illustration and description. The description is not intended to limit the invention to the form disclosed herein. Variations and modifications commensurate with the above are considered to be within the scope of the present invention. The embodiment described herein is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

The invention claimed is:

1. A transvaginal sensor for measuring one or more blood analyte levels or one or more hemodynamic parameters in a tissue-under-test, comprising:
    a light emitter for delivery of light to a tissue-under-test,
    a photodetector for reception of light from the tissue-under-test,
    a sensor body,
    a needle attached to the sensor body designed to adhere the sensor body to the tissue-under-test,
    the needle housing one of the light emitter for subcutaneous delivery of light to the tissue-under-test or the photodetector for subcutaneous reception of light from the tissue-under-test,
    a deployable member housing the other of the light emitter to deliver light to the tissue-under-test or the photodetector to receive light from the tissue-under-test, the deployable member movably attached to the sensor body, the other of the photodetector or light emitter housed in the deployable member set at a distance from the one of the photodetector or light emitter housed in the needle that is greater than a distance from any point on the tissue-under-test contacting surface of the sensor body to the photodetector or light emitter housed in the needle when the sensor is in a deployed state, and
    a plurality of conductors for conducting signals to the light emitter and from the photodetector.

2. The sensor of claim 1 wherein the deployable member has a non-deployed and a deployed state.

3. The sensor of claim 2 wherein the deployable member, positioned in the non-deployed state, causes the sensor to have a smaller cross sectional area than the sensor does with the deployable member in the deployed state.

4. The sensor of claim 1 wherein the deployable member is configured to separate maternal and fetal tissues as the deployable member is deployed.

5. The sensor of claim 2 wherein the deployable member, when in the deployed state, applies a spring force against a tissue-under-test.

6. The sensor of claim 1 wherein the needle attached to the sensor body is a helical needle.

7. The sensor of claim 1 including at least two deployable members.

8. The sensor of claim 1 wherein the deployable member is made of a shape memory alloy.

9. A transvaginal sensor for measuring one or more blood analyte levels or one or more hemodynamic parameters in a tissue-under-test, comprising:
    a light emitter for subcutaneous delivery of light to a tissue-under-test,
    a photodetector for conversion of light received from the tissue-under-test into an electronic signal,
    a sensor body designed to incorporate a helical needle to adhere to the tissue-under-test, the helical needle designed to incorporate the light emitter,
    a deployable member housing the photodetector, the photodetector housed in the deployable member at a distance from the light emitter greater than about one cm when the sensor is affixed to the tissue-under-test, the deployable member movably attached to the sensor body, and
    a plurality of conductors for conducting signals to the light emitter and from the photodetector.

10. A method for sensing one or more blood analyte levels or one or more hemodynamic parameters in a tissue-under-test, comprising the steps of: providing a light emitter in a sensor to emit light into a tissue-under-test, providing a needle affixed to the sensor to house the light emitter and to emit light subcutaneously to the tissue-under-test, movably attaching a deployable member to the sensor, providing a photodetector for reception of light from the tissue-under-test, housing the photodetector in the deployable member, positioning the photodetector in the deployable member to provide a pathlength from the light emitter of at least one centimeter when the sensor is in a deployed state, inserting the sensor transvaginally to the tissue-under-test, deploying the deployable member against the tissue-under-test, conducting at least one of electrical and optical signals to the light emitter and from the photodetector through a plurality of conductors.

11. The method of claim 10 further comprising the step of increasing a cross sectional area of the sensor as the deployable member changes from a non-deployed state to a deployed state.

12. The method of claim 10 further comprising the step of separating maternal and fetal tissues during deployment of the deployable member.

13. The method of claim 11 further comprising the step of applying a spring force against a tissue-under-test when the deployable member is in the deployed state.

14. The method of claim 10 wherein the needle is a helical needle.

15. The method of claim 10 further comprising the step of movably attaching at least two deployable members to the sensor.

16. The method of claim 10 further comprising the step making the deployable member of a shape memory alloy.

17. The method of claim 16 further comprising the step of selecting a shape memory alloy material for a phase change temperature between 27 and 37 degrees Celsius.

18. A method for sensing one or more blood analyte levels or one or more hemodynamic parameters in a tissue-under-test, comprising the steps of:

provided a helical needle in a sensor for adhering to a tissue-under-test, housing a light emitter in the helical needle to emit light subcutaneously into the tissue-under-test and to adhere the sensor to the tissue-under-test, movably attaching a deployable member to the sensor, housing a photodetector in the deployable member to receive light from the tissue-under-test, selecting the position of housing of the photodetector in the deployable member to provide a distance between the photodetector and the light emitter greater than about one centimeter when the sensor is affixed to the tissue-under-test, passing the sensor transvaginally to the tissue-under-test, and deploying the deployable member against the tissue-under-test.

* * * * *

UNITED STATES PATENT AND TRADEMARK OFFICE
CERTIFICATE OF CORRECTION

| | | |
|---|---|---|
| PATENT NO. | : 8,078,251 B2 | Page 1 of 1 |
| APPLICATION NO. | : 11/473092 | |
| DATED | : December 13, 2011 | |
| INVENTOR(S) | : Jonas Alexander Pologe et al. | |

It is certified that error appears in the above-identified patent and that said Letters Patent is hereby corrected as shown below:

The Title of the patent is currently in error. There is an extra "R" in one word. Please change the following word in the title from:

Photoplethysmorgraphic to:

Photoplethysmographic

Signed and Sealed this
Seventh Day of February, 2012

David J. Kappos
*Director of the United States Patent and Trademark Office*